United States Patent [19]

Hochmair et al.

[11] Patent Number: 4,577,641
[45] Date of Patent: Mar. 25, 1986

[54] METHOD OF FITTING HEARING PROSTHESIS TO A PATIENT HAVING IMPAIRED HEARING

[76] Inventors: Ingeborg J. Hochmair; Erwin S. Hochmair, both of A-1130 Wien Jaunerstrafse 27, Vienna, Austria

[21] Appl. No.: 509,239

[22] Filed: Jun. 29, 1983

[51] Int. Cl.$^4$ .................. A61N 1/36; H04R 25/00
[52] U.S. Cl. ........................... 128/746; 179/107 R; 128/1 R
[58] Field of Search .................. 128/746, 904, 419 R, 128/1 R, 784; 179/107 E, 107 BL, 107 R; 73/585; 181/130, 135

[56] References Cited

U.S. PATENT DOCUMENTS

| | | | |
|---|---|---|---|
| 3,848,091 | 11/1974 | Stearns et al. | 73/585 |
| 3,989,904 | 11/1976 | Rohrer et al. | 179/107 R |
| 4,065,647 | 12/1977 | Frye et al. | 179/107 R |
| 4,346,268 | 8/1982 | Geerling | 179/107 R |
| 4,390,748 | 6/1983 | Zwicker | 128/746 |
| 4,400,590 | 8/1983 | Michelson | 128/784 |
| 4,428,377 | 1/1984 | Zollner et al. | 179/107 R |

*Primary Examiner*—Edward M. Coven
*Attorney, Agent, or Firm*—Flehr, Hohbach, Test, Albritton & Herbert

[57] ABSTRACT

Disclosed is a process of fitting a hearing prosthesis to a deaf or severely hearing impaired patient. The prosthesis is connected to the patient, and a signal is then applied to the prosthesis across an audioband. The frequency response of the prosthesis is adjusted so that the patient detects a desired response to the signal. In one application the prosthesis may include a sound processor driving a transmitter, a transcutaneous receiver, and an implanted electrode. A constant amplitude signal is applied to the sound processor, and the frequency response of the sound processor is adjusted so that the patient detects a generally uniform response to the signal. Other signals can be applied, such as bursts of a sine wave or other periodic wave, and band-filtered noise can be employed with the band center frequency being swept either step-wise or continuously. The transmitter and receiver are first adjusted for normal operating coupling and then a constant amplitude continuous sinusoidal signal, for example, is applied. In a multiple channel system, the signal is applied sequentially to each channel. For each channel, the signal is varied in discrete frequency steps across an audio band, and the frequency response of the transmitter is adjusted so that the patient detects a generally uniform response. The dynamic range is identified at each such frequency step between a threshold level and a discomfort level to establish desired aided thresholds and discomfort levels.

16 Claims, 3 Drawing Figures

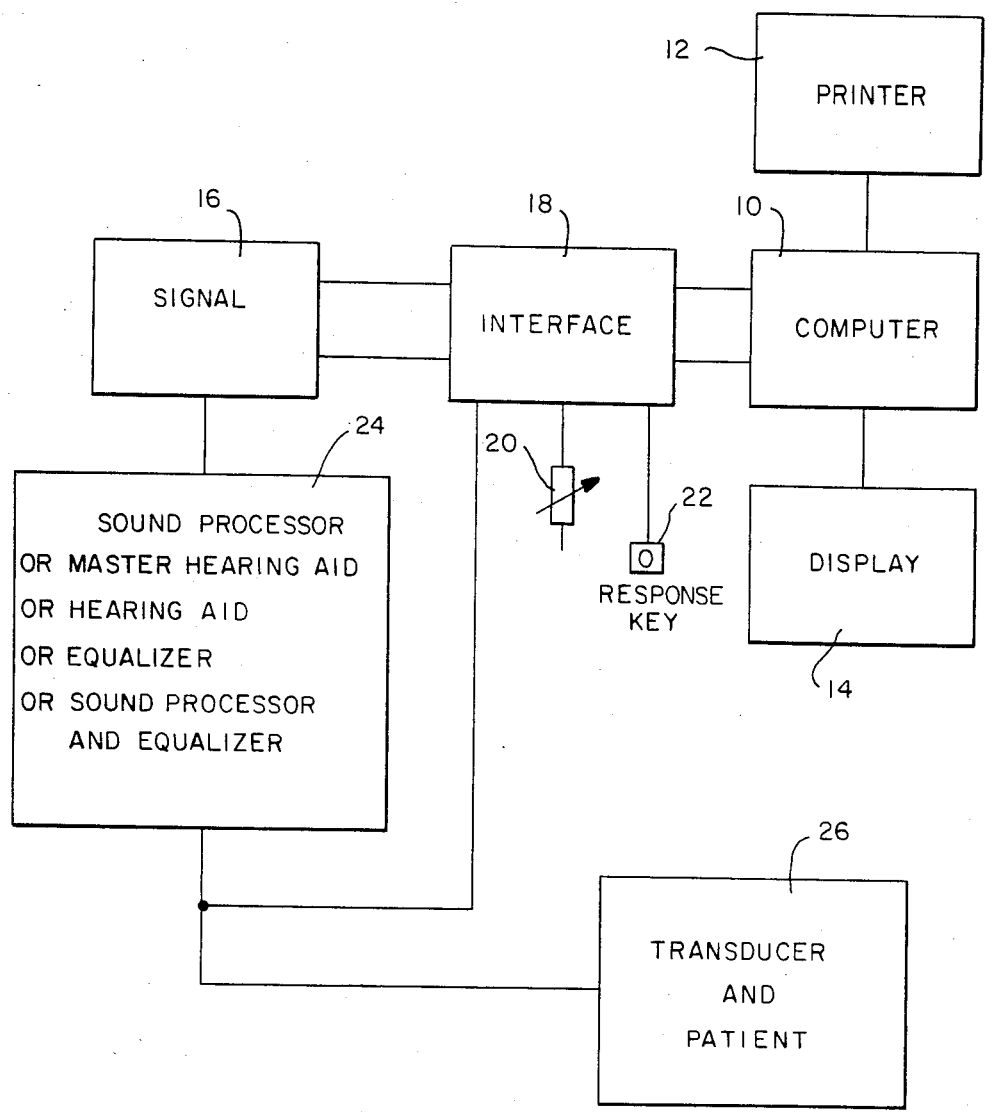
FIG.—1

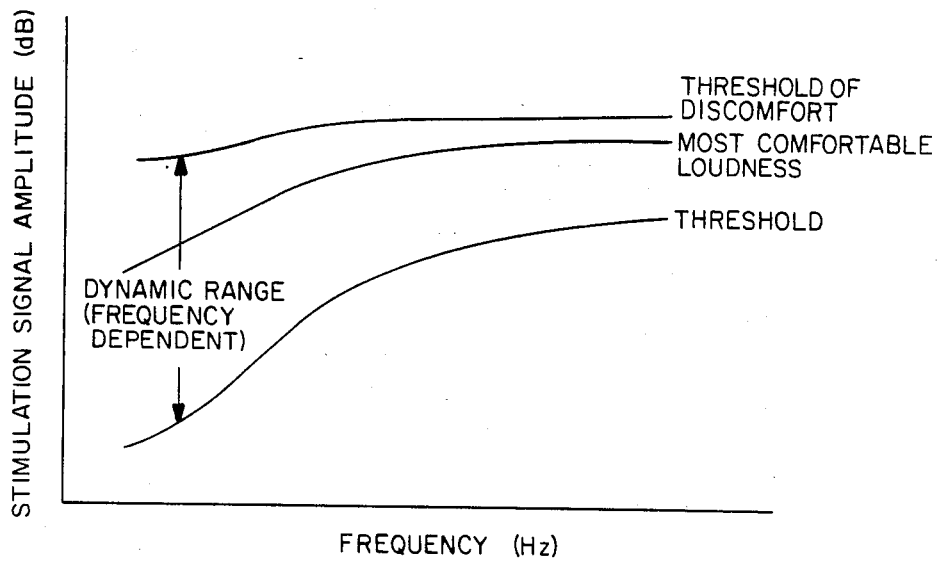
FIG.—2
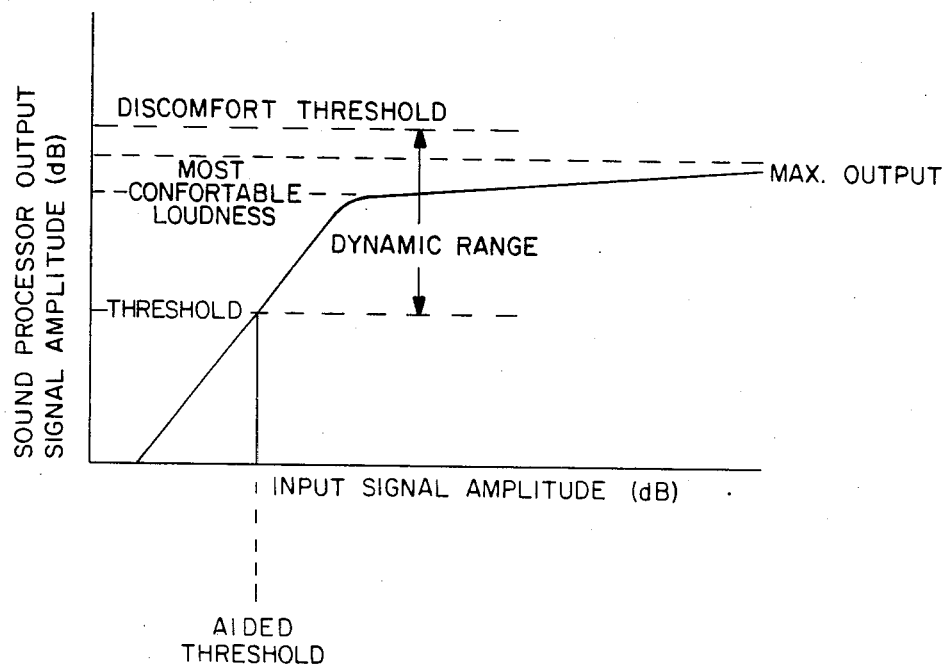
FIG.—3

METHOD OF FITTING HEARING PROSTHESIS TO A PATIENT HAVING IMPAIRED HEARING

This invention relates generally to the fitting of a hearing device to a person having impaired hearing, and more particularly the invention relates to an improved method of fitting a hearing device such as a sound processor driving an implanted electrode to the neural response characteristics of the user.

The use of subcutaneously implanted devices is known. U.S. Pat. No. 3,209,081 discloses a device which is implanted in the mastoid bone. The receiver makes direct contact with the bone through which sound waves are transmitted to the inner ear.

More recently, prosthetic devices have been placed directly in the cochlea or in close proximity to the cochlea for electrical stimulation of the auditory nerve or cochlea. Applicants' U.S. Pat. Nos. 4,284,856 and 4,357,497 disclose a sound processor including multiple channel signal transmission to a subcutaneously implanted receiver for selectively stimulating the cochlea through electrodes in an implanted prosthesis.

The totally deaf or severely hearing impaired persons present a special difficulty in fitting a speech processor. The middle or inner ear may be totally non-responsive to sound waves, but the auditory nerve often can be electrically stimulated to transmit signals to the brain. In the applicants' U.S. Pat. No. 4,284,856 the necessity of isoloudness frequency adjustment and dynamic range compression for the wearer of a cochlear prothesis have been disclosed. Establishing proper sound response characteristics of the auditory nerve in such patients is more critical and difficult to ascertain than is the auditory response of a less severely impaired person. In the latter case, it is conventional to merely establish frequency response of the hearing device which matches the dynamic range of the patient based on an audiogram for the patient.

Accordingly, an object of the present invention is an improved method of fitting a hearing prosthesis to a hearing impaired person.

Another object of the invention is the method of fitting a sound processor driving a subcutaneously implanted receiver and prosthetic electrical structure to a severely hearing impaired person.

A further object of the invention is a method of checking a hearing prosthesis to the needs of a user.

A feature of the invention is the use of tone signals which are frequency swept in increments across a hearing frequency range.

Another feature of the invention is the use of electrical and visual stimulation to establish the proper fitting response of a patient.

In accordance with the invention a fitting process is provided in which frequency response, and, optionally, also maximum output level, transmitter carrier level, and dynamic range compression are established in fitting a hearing device to a hearing impaired user of the device. The method is particularly advantageous with totally deaf and severely hearing impaired individuals, but the process has applicability to other hearing impaired persons requiring a hearing prosthesis.

The invention is readily employed in a single channel auditory stimulation system, as disclosed in applicants' copending patent application Ser. No. 303,547, and in a multichannel sound processor such as disclosed in U.S. Pat. Nos. 4,284,856 and 4,357,497, supra. In the multichannel sound processor the proper coupling of the transmitter and receiver is first established and then each channel is tuned to the preestablished frequency bands. Thereafter, the sound processor is connected to the transmitter and a frequency sweep of the sound processor input is used for adjustment of frequency response to the patient's particular needs. The swept frequency output signal is displayed visually for the patient while the sweep is applied by the transmitter to the receiver and can thus simultaneously be heard by the patient. In a preferred embodiment a continuous sinusoidal signal is provided having a fixed, preselected amplitude. The frequency is swept across an audio range such as from 100 Hz to 3160 Hz preferably in spaced frequency steps. The patient is able to visualize the swept signal by suitable display means, and frequency response adjustment means is used by the patient or operator for varying the frequency response to obtain a response which is generally uniform in loudness across the swept frequency band. The adjustments of frequency response or signal amplitude are made at most comfortable loudness level. The adjustments can also be made at hearing threshold and at threshold of discomfort. Threshold and threshold of discomfort can also be determined using other methods which are implemented in the apparatus used for the fitting method or can be standard methods of psychoacoustics. According to these measurements the compression characteristic is set.

The invention and objects and features thereof will be more readily apparent from the following detailed description and appended claims when taken with the drawing, in which:

FIG. 1 is a functional block diagram of a test system for implementing the fitting process in accordance with the invention.

FIG. 2 is a plot of response characteristics across an audio frequency band to be established for a patient in accordance with the invention.

FIG. 3 is a plot of sound processor output versus signal input illustrating the result of the fitting process for amplitude compression in accordance with the invention.

Before describing an illustrative embodiment, the definitions of relevant terms are given. As used herein and as recognized in the art, a cochlear prosthesis generates electric signals and delivers them to the auditory nerve via an implanted stimulation electrode, thus causing neural stimulation. The cochlear prosthesis basically consists of a sound processor, a transmitter for transcutaneous signal transmission, an implanted receiver/stimulator circuitry, and an implanted single or multiple channel stimulating electrode. Instead of a transmitter and receiver, a percutaneous plug is used in some cases. The sound processor can contain one or several channels of sound processing. The number of sound processing channels can be smaller, equal or greater than the number of stimulating electrodes used.

"Threshold" is the level at which a stimulus becomes detectable.

"Most Comfortable Loudness (MCL)" is the level for best intelligibility and to which one could comfortably listen for an extended period of time.

"Threshold of Discomfort"-"Loudness Discomfort Levels", and "Uncomfortable Loudness Level (ULL)" is the level at which loudness becomes uncomfortable and the sensation could not be tolerated for an extended period of time.

"Sensitivity of Hearing Prothesis" is the input sound level at which the signal-to-noise-ratio at the output of the hearing prothesis equals unity.

"Aided Threshold" is the input sound level at which the patient's threshold when wearing the prosthesis is reached.

"Audio Band" is the whole or a part of frequencies between a lower audio frequency and an upper audio frequency, typically between the range of 17 Hz and 17 KHz.

"Amplitude Compression" is the reduction of the large input signal amplitude range to a lower response range.

In practicing the invention a signal generator for producing an electrical signal which is variable in amplitude and frequency and a visual display of the transmitted signal are required. FIG. 1 is a functional block diagram illustrating a computer controlled test system. The computer 10 (a TRS-80 for example) is connected to a printer 12 for maintaining a record of the test procedure and results and is connected to a display 14 for displaying a transmitted signal and the cumulative frequency response of the patient. The computer 10 controls a signal generator 16 which is interconnected to computer 10 through an interface 18. Connected to the interface 18 is a manually adjustable potentiometer 20 which can be used by the patient or the test operator to manually vary the amplitude of the signal from generator 16. A response key 22 is provided to signal back to the computer whether the stimulation signal is heard or not.

The signal from generator 16 is applied to the sound processor 24 which couples the test signals to the transducer and patient 26. The signal from the output of the sound processor is also fed back to the computer via the interface 18. In a multichannel sound processor as described in the patents referenced above, a plurality of signals are transmitted through several channels, and the received signals are then applied through a multiple lead output to a prosthetic multielectrode device which is implanted in the cochlea. If a hearing aid has to be checked, the test signal is applied to the patient wearing the aid via a loudspeaker in a soundproof room. If the parameters for fitting a hearing aid to a patient have to be measured, the signal is fed to a master hearing aid or an equalizer which is connected to headphones or a loudspeaker. When a sound processor is to be fitted to a patient, the sound processor is coupled to the implant via the transmitter of the sound processor. To check the fitting of a sound processor, the sound processor with or without an equalizer in series is coupled to the implant via the transmitter. If the parameters for fitting a sound processor to a patient have to be measured, an equalizer is coupled to the implant via the transmitter.

Before the test begins, a transcutaneous transmission is optimized by proper positioning of the output coils of the transmitter with respect to the coils of the receiver as described in applicants' co-pending application Ser. No. 303,590 filed Sept. 18, 1981, now U.S. Pat. No. 4,441,210, issued Apr. 3, 1984. Thereafter, signals are generated and applied to the sound processor. The generated signals are preferably a continuous sinusoidal wave and the signals are applied to the sound processor in incremental frequency steps. For example, the frequency may be swept from 100 Hz to 3160 Hz in 90 logarithmically equally spaced frequency steps. When all 90 steps are used, the total time for the frequency sweep upwards and downwards again is approximately 11 seconds. In case only every other frequency is used, the total time for the sweep is reduced by half. By generating the signal in steps, the patient can more readily compare and equate his response to the signals at the various frequencies.

The swept frequency output signal is displayed visually for the user while the signal is applied by the transmitter to the receiver and thus simultaneously heard by the user. The user can then use both the visual and audio stimulation to determine his response to the signal and thus permit adjustment of the frequency response of the hearing prosthesis. One preferred end result is the establishment of a generally uniform response, in loudness and quality, by the patient to input signals across the frequency spectrum of interest (e.g. 100 to 3160 Hz) at most comfortable loudness (which is shown in relation to threshold and threshold of discomfort in FIG. 2 in the drawing).

With certain patients it may be necessary to use different sizes of frequency steps and/or different sweep times. Bursted signals instead of continuous signals might be used. Also, bandfiltered noise with the bandfilter varying in center frequency in a similar way as described for the sinewave can be used.

After the generally uniform frequency response iso-loudness frequency adjustment is established, a dynamic range compression may be established at the various frequency levels, as illustrated in FIG. 3 of the drawing for one particular frequency. The dynamic range (e.g. amplitude ratio between the threshold level and threshold of discomfort level) will establish the amplitude compression characteristic needed by the sound processor for the patient. The amplitude compression is either kept independent of frequency or is made dependent on frequency according to the measured range between threshold and most comfortable loudness level. The acoustic aided thresholds of the patient can such be set to values between 20 and 60 db SPL over the speech frequency band.

Importantly, during the testing of the patient to establish uniform stimulation across the frequency spectrum and to establish gain settings at each frequency increment, the patient is able to point to the visual display thereby giving the operator an indication of the signal level for minimum stimulation (threshold) and the level for causing discomfort. A printer will be plotting the frequency response after the adjustment of frequency equalization and while adjusting the dynamic range to transfer characteristics plotted.

A similar testing procedure can be employed for psychophysically testing persons prior to the implantation of a cochlear prosthesis in order to select patients who would most benefit from such a procedure. A primary difference in the testing procedure is that the electrical current must be delivered directly to the cochlea as the stimulant instead of as a stimulus delivered through the sound processor. A metallic needle placed transtympanically on the promontory or at least in close proximity to the round window activated through an isolated current source is used to preoperatively deliver the electrical stimulus to the cochlea. The same series of tests can be performed post operatively also after the implantation of a cochlear implant via a transcutaneous signal link instead of the transtympanic needle. This will be done for comparison to data collected pre-operatively and for followup purposes.

The fitting procedure is particularly advantageous with a sound processor utilizing an implanted prosthesis, however, the same procedure can be employed with patients having less severe hearing impairment using a hearing aid.

While a computer controlled signal generator is preferably used in producing the sweep for test purposes, other signal sources such as a frequency synthesizer or tracking oscillator can be used for generating the electrical signals. While the stimulation signals are preferably in spaced frequency steps, the sweep can be a continuous sine wave or other periodic signal. Alternatively, the signals can be a sweep of bursts of a sine wave or other periodic signal. Band-filtered noise can be employed where the band center frequency is swept either step-wise or continuously.

Thus, while the invention has been described with respect to a particular embodiment and application, the description is illustrative of the invention and is not to be construed as limiting the invention. Various modifications and applications may occur to those skilled in the art without departing from the true spirit and scope of the invention as defined by the appended claims.

What is claimed is:

1. A method of fitting a hearing prosthesis to a hearing impaired user comprising the steps of
    connecting said hearing prosthesis to the user,
    applying a signal to said hearing prosthesis,
    sweeping said signal in discrete frequency steps,
    visually displaying said signal as transmitted by said hearing prosthesis for user observation as the frequency thereof is varied,
    determining user response to said signal at each of said discrete frequency steps as the user observes the visual display, and
    adjusting frequency response of said hearing prosthesis so that the user detects a desired response to said signal at each frequency step.

2. The method as defined by claim 1 wherein said signal is a sinusoidal wave.

3. The method as defined by claim 1 wherein said signal is continuous and has a constant average amplitude.

4. The method as defined by claim 1 and further including the steps of adjusting compression characteristics of said hearing prosthesis at said frequency steps to establish desired aided thresholds and discomfort levels.

5. The method as defined by claim 4 wherein said hearing prosthesis comprises a sound processor driving an implanted electrode.

6. The method as defined by claim 5 wherein said hearing prosthesis comprises a multichannel sound processor driving an implanted electrode, and said steps are carried out for each channel.

7. The method as defined by claim 1 wherein said hearing prosthesis comprises a sound processor driving an implanted electrode.

8. The method as defined by claim 7 wherein said hearing prosthesis comprises a multichannel sound processor driving an implanted electrode, and said steps are carried out for each channel.

9. A method of fitting a sound processor driving a transmitter, a transcutaneous receiver, and implanted electrode means to a user having severe hearing impairment comprising the steps of
    connecting said sound processor to a user through said transcutaneous receiver and implanted electrode means,
    adjusting said transmitter and said receiver for normal operating coupling,
    applying a signal to said sound processor whose frequency is swept across an audio band,
    visually displaying said signal as transmitted by said transmitter for user observation as the frequency thereof is varied,
    determining user response to said signal as the user observes the visual display, and
    adjusting the frequency response of said sound processor so that the patient detects a desired response to said signal across said audio band.

10. The method as defined by claim 9 wherein said signal is a continuous sinusoidal wave.

11. The method as defined by claim 9 and further including the step of adjusting compression characteristics of said sound processor at a plurality of frequencies to establish desired aided thresholds and discomfort levels.

12. The method as defined by claim 11 wherein said transmitter and said receiver have multiple channels, and said steps are carried out for each channel.

13. The method as defined by claim 9 wherein said transmitter and said receiver have multiple channels, and said steps are carried out for each channel.

14. A method of checking a hearing prosthesis comprising the steps of
    connecting said hearing prosthesis to the user,
    applying a signal to said hearing prosthesis whose frequency is swept across an audio band in discrete frequency steps,
    visually displaying said signal as transmitted by said hearing prosthesis for user observation as the frequency thereof is varied, and
    determining user response to said signal as the user observes the visual display.

15. The method as defined by claim 14 wherein said signal is a sinusoidal wave.

16. The method as defined by claim 15 wherein said signal is continuous and has a constant average amplitude.

* * * * *